United States Patent
Carpenter (10) Patent No.: US 8,547,550 B2
(45) Date of Patent: Oct. 1, 2013

(54) BIOLOGICAL AND CHEMICAL COLLECTION AND DETECTION

(75) Inventor: Jeffrey P. Carpenter, Lancaster, OH (US)

(73) Assignee: Battelle Memorial Institute, Columbus, OH (US)

( * ) Notice: Subject to any disclaimer, the term of this patent is extended or adjusted under 35 U.S.C. 154(b) by 2 days.

(21) Appl. No.: 13/260,973

(22) PCT Filed: Mar. 26, 2010

(86) PCT No.: PCT/US2010/028869
§ 371 (c)(1),
(2), (4) Date: Sep. 29, 2011

(87) PCT Pub. No.: WO2010/114772
PCT Pub. Date: Oct. 7, 2010

(65) Prior Publication Data
US 2012/0040330 A1 Feb. 16, 2012

Related U.S. Application Data

(60) Provisional application No. 61/166,399, filed on Apr. 3, 2009.

(51) Int. Cl.
*G01J 3/28* (2006.01)
(52) U.S. Cl.
USPC .......................................... 356/326; 356/300
(58) Field of Classification Search
USPC ................................................ 356/300–334
See application file for complete search history.

(56) References Cited

U.S. PATENT DOCUMENTS

| 5,518,883 | A | 5/1996 | Soini |
| 5,701,012 | A * | 12/1997 | Ho .............................. 250/461.2 |
| 5,891,738 | A | 4/1999 | Soini et al. |
| 7,428,045 | B2 * | 9/2008 | Stewart et al. ................ 356/301 |
| 2006/0269923 | A1 | 11/2006 | Trotta |
| 2007/0087430 | A1 * | 4/2007 | Siegel et al. ............... 435/287.2 |
| 2008/0274489 | A1 * | 11/2008 | Siegel et al. .................... 435/28 |

FOREIGN PATENT DOCUMENTS

| EP | 1624071 A2 | 2/2006 |
| WO | 2007/021485 A2 | 2/2007 |

OTHER PUBLICATIONS

Notification of Transmittal of the International Preliminary Report on Patentability for PCT Application No. PCT/US2010/028869, mailing date of Oct. 18, 2011; International Preliminary Report on Patentability, European Patent Office, Rijswijk, Netherlands.

(Continued)

*Primary Examiner* — Tara S Pajoohi Gomez
(74) *Attorney, Agent, or Firm* — Thomas E. Lees, LLC (57) ABSTRACT

A fluorescence-cued Raman identification system comprises a collection subsystem to collect samples, a reagent treatment subsystem to treat collected samples and a fluorescence imaging subsystem that automatically takes at least one image of the collected sample. The subsystems further include a Raman spectroscopy subsystem that measures the spectrum of viable organisms located from at least one collected image, a visible imaging microscope subsystem that provides a visual image of the particle analyzed by the Raman spectroscopy subsystem and a processor configured to perform image processing to locate viable organisms within the sample, which are targeted by the Raman spectroscopy subsystem. The processor further analyzes the spectrum recorded by the Raman spectroscopy subsystem to make a preliminary identification of the targeted organisms, which can be verified by an operator using the visible imaging microscope subsystem.

20 Claims, 3 Drawing Sheets

(56) References Cited

OTHER PUBLICATIONS

J. Noh et al., "Combined micro-Raman/UV-visible/fluorescence spectrometer for high-throughput analysis of microsamples." Review of Scientific Instruments, vol. 78, 2007, pp. 72205-1 to 72205-6, XP002599773, College Park, MD USA.
Written Opinion of the International Preliminary Examining Authority for PCT Application No. PCT/US2010/028869; Mailing Date of Aug. 2, 2011; European Patent Office, Rijswijk, The Netherlands.
Notification of Transmittal of the International Search Report and the Written Opinion of the International Searching Authority for PCT Application No. PCT/US2010/028869; Mailing Date of Sep. 28, 2010; European Patent Office, Rijswijk, The Netherlands.
Japanese Office Action dated Jul. 2, 2013 for Japanese Patent Application No. 2012-503533, filed Sep. 28, 2011; on page one of the Japanese Office action.
Rosch, Petra et al., "Fast and Reliable Identification of Microorganisms by Means of Raman Spectroscopy", Proc. SPIE, 2007, vol. 6633, p. 66331A.1-66331A.9.

* cited by examiner

BIOLOGICAL AND CHEMICAL COLLECTION AND DETECTION

CROSS REFERENCE TO RELATED APPLICATIONS

This application is a national stage entry under 35 U.S.C. §371 of International Application No. PCT/US2010/028869, filed Mar. 26, 2010, entitled "BIOLOGICAL AND CHEMICAL COLLECTION AND DETECTION," which claims the benefit of U.S. Provisional Patent Application Ser. No. 61/166,399, filed Apr. 3, 2009, entitled "BIOLOGICAL AND CHEMICAL COLLECTION AND DETECTION," the disclosures of which are hereby incorporated by reference.

BACKGROUND

The present invention relates in general to Raman identification of particles and in particular, to fluorescence-cued Raman identification of viable organisms.

Standard microbiological methods developed to determine whether bacterial cells are dead or alive generally rely upon the ability of the tested bacterial cells to grow and produce colonies as a measure of the viability of the bacterial cells under test. However, industries such as the pharmaceutical industry are concerned about the identification of viable particles including organisms that are viable, but non-culturable. For example, certain bacteria may go into a viable but non-culturable state wherein the bacterial organisms have metabolic processes but are not undergoing cell division. In this state, bacteria are still viable, but may not be shown as colony forming units under nonselective growth conditions using common techniques such as conventional plate counts. Such viable but non-culturable bacteria may comprise a concern, for example, in public health risk assessments because certain pathogenic bacteria may be able to transition between a viable but non-culturable state and an infectious state.

BRIEF SUMMARY

According to various aspects of the present invention, a method of identifying organisms of interest comprises collecting a sample, such as an environmental sample or product sample. The method further comprises treating the collected sample with a reagent that identifies whether there are any organisms of interest within the collected sample. In this regard, a potential viable organism of interest, such as a viable cell, is distinguishable based at least in part, by a marker produced as a result of a reaction between the reagent and the potential viable organism of interest. The reagent may include for example, a viability stain that fluoresces when activated by a cell's processes, a reporter dye, an assay that renders any living organism detectable, etc.

The method further comprises collecting image data of the sample using a microscope, e.g., by transferring the sample to an automated microscope stage and using the microscope stage to collect images of the sample, and locating any potential viable organisms of interest within the collected sample by utilizing image processing to automatically locate whether there are occurrences of the marker within at least one image of the collected sample.

Still further, the method comprises identifying at least one target location within the sample for spectral interrogation of a potential viable organism, each target location selected based upon the location of a corresponding instance of the marker within the sample that is derived from the collected image data. The method also further comprises obtaining spectral information of each identified target location within the sample, analyzing any obtained spectral information to automatically establish a preliminary identification of at least one corresponding located potential viable organism, each preliminary identification made to at least a small ambiguity of the identification and providing information related to the result of the preliminary identification for a final confirmation by a user.

According to further aspects of the present invention, a system for identifying organisms comprises a plurality of subsystems that cooperate to implement a fluorescence-cued Raman identification system. The subsystems include a collection subsystem that collects a sample onto a filter and a reagent treatment subsystem that receives the sample from the collection subsystem and treats the sample collected by the collection subsystem using a reagent that identifies whether there are any organisms of interest within the sample, where a potential viable organism of interest is distinguishable based at least in part, by a marker produced as a result of a reaction between the reagent and the potential viable organism of interest. The subsystems further comprise a fluorescence imaging subsystem that receives the treated sample from the reagent treatment subsystem and that automatically takes at least one image of the collected sample.

The subsystems further include a Raman spectroscopy subsystem that receives the sample from the fluorescence subsystem and that measures the spectrum of potential viable organisms that are located based upon at least one image of the collected sample and a visible imaging microscope subsystem that provides a visual image of any organisms analyzed by the Raman spectroscopy subsystem. The system further comprises a processor that performs image processing to locate potential viable organisms within the sample, which are targeted by the Raman spectroscopy subsystem. The processor further analyzes the spectrum recorded by the Raman spectroscopy subsystem to make a preliminary identification of the targeted organisms for confirmation by a user using the visible imaging microscope subsystem.

BRIEF DESCRIPTION OF THE SEVERAL VIEWS OF THE DRAWINGS

The following detailed description of various aspects of the present invention can be best understood when read in conjunction with the following drawings, where like structure is indicated with like reference numerals, and in which.

DETAILED DESCRIPTION

According to various aspects of the present invention, a fluorescence-cued Raman identification system is provided that utilizes fluorescence assays to detect one or more organisms of interest. The fluorescence assay may be a general assay for all/multiple types of viable organisms or alternatively, a specialized assay for targeting a specific organism or organisms.

In general, the above fluorescence assays, including non-specific assays, may be utilized to target viable organisms, such as viable cells, in either spore or vegetative states within collected samples. For example, a selected chemical fluorescence assay may be used for targeting viable organisms collected in a sample. The reaction of specific locations within the sample to the chemical fluorescence assay is used to select out and target regions of the collected sample that are of interest for further interrogation. Spectral data is collected from the targeted sample regions that were selected from within the larger sample for identification, e.g., using a Raman spectrometer. The spectral data collected from the targeted interrogation is evaluated to generate an unambiguous identification of the targeted organism(s). Alternatively, the evaluation of the spectral data may result in an identification of the targeted organism(s) within a small ambiguity group.

The system may then present information related to the targeted interrogation to a human operator for verification and/or interpretation of the machine implemented operations. For instance, in an exemplary implementation, the system presents information related to any cells that were detected or otherwise classified as viable or likely viable within a small ambiguity group to an operator. The information presented by the system to a human operator for their concurrence with the machine identification, may take the form of a microscope or other visual image or images of the cells judged by the system to be viable or likely viable. Thus, for example, microbiologists may be able to conduct rapid, objective determinations as to whether or not a sample is likely to contain viable organisms.

Figure 1:
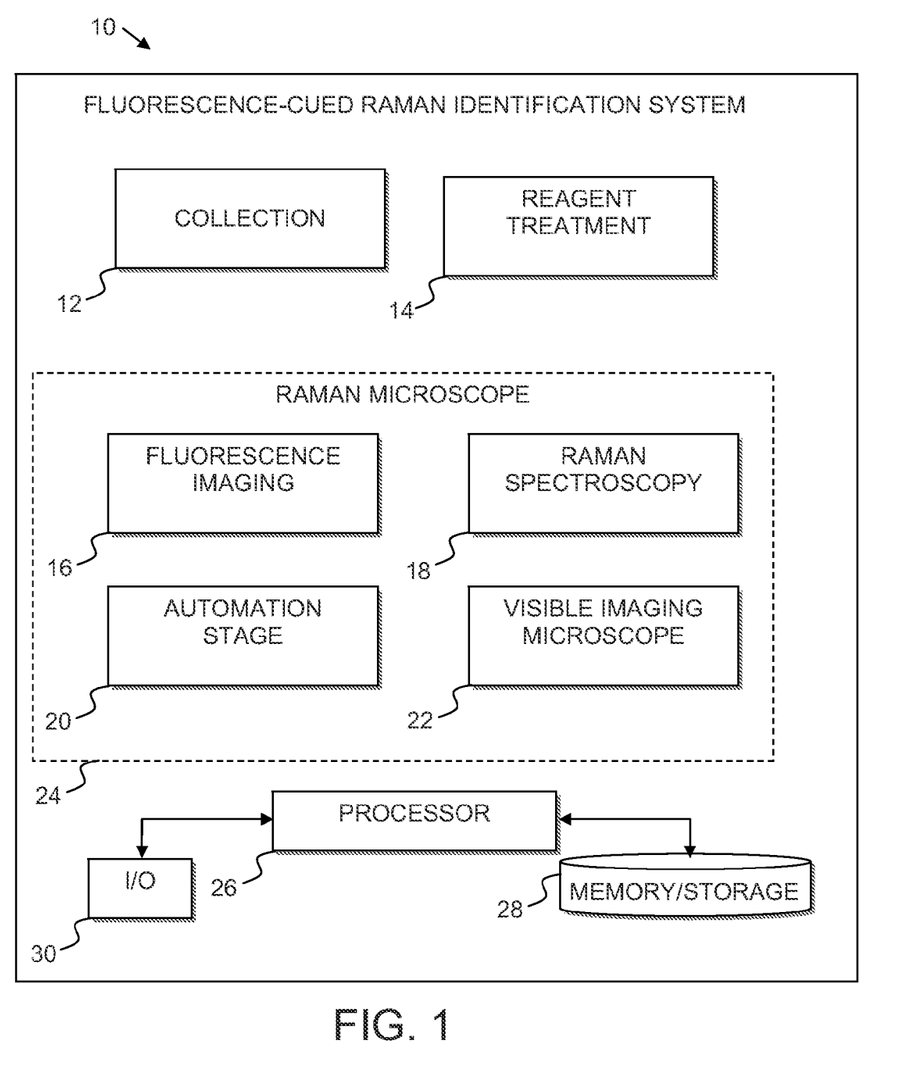
FIG. 1 is a schematic illustration of a fluorescence-cued Raman identification system for the identification of viable organisms according to various aspects of the present invention.

Referring now to the drawings and in particular to FIG. 1, a fluorescence-cued Raman identification system 10 is illustrated according to various aspects of the present invention. The fluorescence-cued Raman identification system 10 includes, in general, a plurality of subsystems that cooperate to implement the functionality of fluorescence-cued Raman identification as described more fully herein. As an example, the illustrated system 10 includes six subsystems including a collection subsystem 12, a reagent treatment subsystem 14, a fluorescence imaging subsystem 16, a Raman spectroscopy subsystem 18, an automated stage subsystem 20, and a visible imaging microscope subsystem 22.

In practical implementations of various aspects of the present invention, the various logical and functional features of two or more subsystems may be combined, consolidated or otherwise integrated into a common physical structure. For example, in an exemplary implementation, the fluorescence imaging subsystem 16, the Raman spectroscopy subsystem 18, the automated stage subsystem 20, and the visible imaging microscope subsystem 22 are integrated into a Raman microscope system 24. Other logical and/or physical groupings of the various subsystems may also be implemented, depending for example, upon the particular implementation. Additionally, a processor 26 is optionally included, e.g., as a processing device that is integrated or otherwise in communication various subsystems of the system 10.

In an exemplary implementation, the collection subsystem 12 collects a sample onto a filter. The reagent treatment subsystem 14 receives the sample from the collection subsystem 12 and treats the sample collected by the collection subsystem 12 using a reagent that identifies whether there are any organisms of interest within the sample. In this regard a potential viable organism of interest is distinguishable based at least in part, by a marker produced as a result of a reaction between the reagent and the potential viable organism of interest. The fluorescence imaging subsystem 16 receives the treated sample from the reagent treatment subsystem 14 and automatically takes at least one image of the collected sample. The Raman spectroscopy subsystem 18 receives the sample from the fluorescence subsystem 16 and measures the spectrum of potential viable organisms that are located based upon at least one image of the collected sample. The visible imaging microscope subsystem 22 provides a visual image of any organisms analyzed by the Raman spectroscopy subsystem 18.

The automation stage that automatically transports the filter between at least two subsystems. Further, the processor 26 performs image processing to locate potential viable organisms within the sample, which are targeted by the Raman spectroscopy subsystem 18. The processor 26 further analyzes the spectrum recorded by the Raman spectroscopy subsystem 18 to make a preliminary identification of the targeted organisms for confirmation by a user using the visible imaging microscope subsystem 22.

The processor 26 performs the necessary processing, e.g., to control one or more of the hardware components of the system 10, to perform software processing, classification, analysis, image processing, data management, etc. The processor 26 is also capable of direct or indirect communication with other devices, circuits or other processes, such as memory 28 and input output (I/O) 30. Thus, the processor 26 can communicate image data, spectral data, preliminary identification information etc., to external sources, as will be described in greater detail herein.

Although schematically illustrated as a single block 28 in the block diagram of FIG. 1, in practice, the memory 28 can be implemented as any combination of one or more computer readable storage medium(s) having computer readable program code embodied therewith. In this regard, the computer readable storage medium is implemented as a tangible medium to contain or store a program, data or other information for use by or in connection with an instruction execution system, apparatus, or device, e.g., the processor 26 for carrying out operations described more fully herein. Each computer readable storage medium may utilize, for example, an electronic, magnetic, optical, electromagnetic, infrared, or semiconductor or any suitable technology or combination of technologies. Moreover, the memory 28 may be implemented as a hard disk, a random access memory (RAM), a read-only memory (ROM), an erasable programmable read-only memory (EPROM or Flash memory), a portable compact disc read-only memory (CD-ROM), an optical storage device, a magnetic storage device, etc.

The I/O 30 facilitates interaction with users and/or other electronic devices. Exemplary I/O 30 may include a network interface or other adapter to facilitate communication with other electronic devices, e.g., across a network. Exemplary I/O 30 further comprises devices and circuits for interacting with a user, such as a display screen, video adapter, keypad or keyboard, mouse or other pointing device, keypad/mouse adapter, etc.

In an exemplary implementation, the processor 26 executes computer program instructions, e.g., stored in the memory 28, to perform image processing of image data collected by the fluorescence imaging subsystem 16 to locate viable organisms within a collected sample. Based upon the results of the image processing, the processor 26 defines targeted regions within the collected image data. The target region information defined by the processor 26 is utilized by the Raman spectroscopy subsystem 26 to collect Raman spectral data by performing targeted interrogation of the collected sample at the targeted region(s). The processor 26 then executes computer program code to analyze the spectral information recorded by the Raman spectroscopy subsystem 24 to make a preliminary identification of the targeted organisms, etc., as will be described in greater detail herein. In this regard, the processor 26 may interact with memory/storage 28 and/or I/O 30 to retrieve program code, data files, classifiers, control parameters or any other information or program code necessary to perform functions as set out in greater detail herein.

Figure 2:
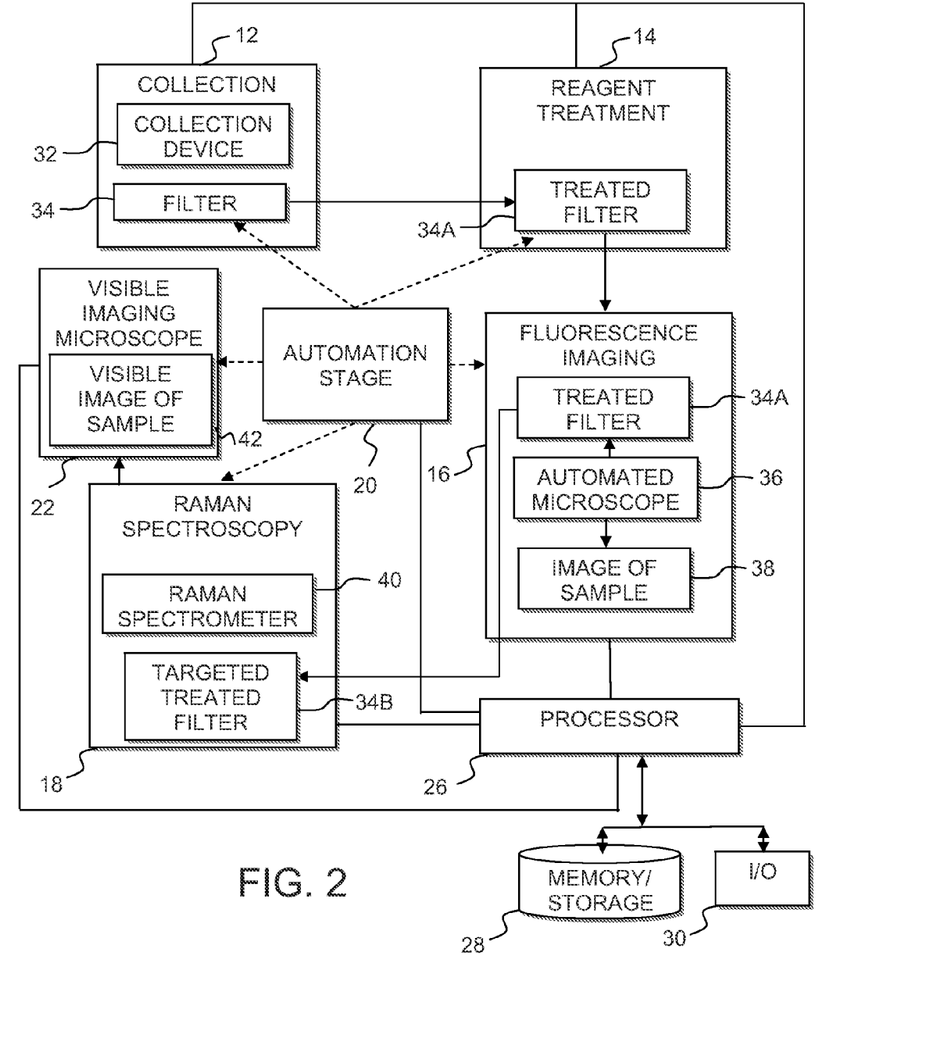
FIG. 2 is a flow diagram of the fluorescence-cued Raman identification system of FIG. 1, according to various aspects of the present invention.

Referring to FIG. 2, an exemplary implementation of the system 10 of FIG. 1 is illustrated according to various aspects of the present invention. During operation, the collection subsystem 12 collects a sample onto a sample substrate. In an exemplary implementation, the collection subsystem 12 utilizes a collection device 32 to collect a sample onto an appropriate sample substrate, e.g., a filter. The collection device 32 may comprise, for example, an aerosol collector, solid surface small area impactor, electrostatic precipitation device, cyclone device or other collection technology. In an illustrative example, the collection device 32 draws and accelerates a fluid stream, such as from the ambient air, through the collector. Particulate matter that is entrained in the stream is extracted and deposited onto the sample substrate, e.g., the filter 34 in a relatively small, defined sample area. The filter 34 is any suitable substrate or other arrangement for holding a collected sample. For instance, the filter 34 can be implemented as a non-Raman active membrane filter 34. However, in practice, the sample substrate may comprise other forms of sample containing material.

Moreover, in certain exemplary implementations, the filter 34 is manually placed in the collection subsystem 12. In alternative exemplary implementations, the filter 34 is automatically placed in the collection subsystem 12, e.g., via a translation feature of the automation subsystem 20. For instance, the automation subsystem 20 can utilize an automation mechanism to retrieve a filter 34, e.g., from a substrate storage area or other location, and transport the filter 34 to the collection device 32. In this regard, the automation stage 20 utilizes a rotational stage, linear stage or other arrangement of features to transport the filter 34 between one or more of the subsystems as described more fully herein. The processor 26 can control the automation stage 20, e.g., to establish the timing and flow of the filter 34 through the system 10.

In one exemplary application, the system 10 is configured to sample the air for particulates that fall within a range of sizes that can be inhaled. For example, the biological and chemical detection system 10 may be used to discriminate nitrate and sulfate, ammonium, fungal spores and other particulates in collected samples. As such, the collection device 32, e.g., a small area collector, is designed to collect and deposit particulates generally within the size range of approximately 1 µm to 10 µm on the filter 34. In alternative exemplary implementations, the collection subsystem 12 can collect other types of environmental samples, such as water samples, product samples, process samples, etc., using appropriate sampling techniques. As such, the particular collection subsystem implementation may vary, depending for example, upon the type of sample to be collected.

Upon collection of a sample by the collection device 32, the filter 34 carrying the collected sample is relocated to the reagent treatment subsystem 14. In exemplary implementations, the relocation of the filter 34 may be carried out automatically via translation by the automation subsystem 20 e.g., using a linear translation stage, a rotational translation stage, etc. In alternative exemplary implementations, the reagent treatment subsystem 14 may otherwise receive the sample from the collection subsystem 12, e.g., via manual relocation. Regardless, the reagent treatment subsystem 14 treats the samples collected by the collection subsystem 12 using reagents that identify organisms collected onto the filter 34. For example, the sample on the filter 34 is treated at the reagent treatment subsystem 14, using a reagent and/or equipment, such as from a vendor such as AES Chemunex, Inc., of Princeton N.J., USA; MicroLink (Milliflex) of Cork Ireland or Celsis International, Cambridge United Kingdom.

The treatments cause viable organisms collected on the filter 34 to be distinguishable. For example, a treatment such as a viability stain may cause one or more types of viable organism to emit a glow that is stable for a finite period of time, e.g., several minutes. The treatments may also/alternatively utilize a reporter dye that provides a specific spectral response to a corresponding excitation. While many such assays detect any living organism, certain assays are available that can be targeted at a specific organism or organisms. In this regard, the selection of the specific treatment will depend upon the application and/or organism(s) of interest. For purposes of clarity herein, the filter 34 is identified as a "treated filter 34A" to designate that the sample collected onto the filter 34 has been treated using a reagent.

Upon treatment of the sample by the reagent treatment subsystem 14, the filter 34A is relocated to the fluorescence imaging subsystem 16. In exemplary implementations, the relocation of the filter 34A is carried out automatically via translation by the automation subsystem 20 e.g., using a linear translation stage, a rotational translation stage, etc., in a manner analogous to that described above. In alternative implementations, the fluorescence imaging subsystem 16 may otherwise receive the treated filter 34A, e.g., via manual relocation.

The fluorescence imaging subsystem 16 receives the treated sample on the filter 34A from the reagent treatment subsystem 14 and automatically takes at least one image of the collected sample. For example, an automated microscope stage 36 within the fluorescence imaging subsystem 16 takes at least one focused image 38 of the sample collected on the treated filter 34A. Image processing locates any viable organisms on the treated filter 34 by identifying at least one distinguishing feature that is rendered discoverable by the treatment. In an exemplary implementation, the processor 26 analyzes data corresponding to the one or more images collected by the automated microscope stage 36 of the fluorescence imaging subsystem 16 to identify cells/particles/viable organisms, etc., identified by the marker(s) left behind as a result of treatment at the reagent treatment subsystem 14.

The processor 26 optionally further controls system level operation of the fluorescence imaging subsystem 16, e.g., by instructing the automated microscope when to begin collecting image(s) and/or by instructing the automated microscope 36 as to how many images to collect. For instance, the automated microscope can take at least one image under the control of the processor 26. The processor 26 also optionally controls operational set points, e.g., operating parameters of the automated microscope 36, e.g., by setting or otherwise influencing the magnification, focus, exposure, location within the treated filter 34A, etc. The processor 26 further utilizes image processing to automatically locate whether there are occurrences of the marker within at least one image of the collected sample. In performing such image analysis, the processor 26 can perform data processing, such as image data filtering, processing, classification, statistical analysis, feature or pattern recognition, etc.

Upon imaging of the sample by the fluorescence imaging system 16, the filter 34A is relocated to the Raman spectroscopy system 18. In exemplary implementations, the relocation of the filter 34A is carried out automatically via translation by the automation subsystem 20 e.g., using a linear translation stage or a rotational translation stage. In alternative implementations, the Raman spectroscopy system 18 receives the treated filter 34A, e.g., via manual relocation. Still further, there may not be a need to physically relocate the filter 34, e.g., where both the Fluorescence imaging subsystem 16 and the Raman spectroscopy subsystem 18 can both interact with the filter 34 positioned at a common physical location, e.g., using optics, etc.

The Raman spectroscopy subsystem 18 measures the spectrum of any detected potential viable organisms that are located based upon an analysis of the focused image(s) of the sample collected by the fluorescence imaging subsystem 16. In an exemplary implementation, the processor 26 determines target locations based upon the identification of markers located within at least one image and feeds the necessary coordinates derived from image processing of the image data collected by the fluorescence imaging subsystem 16 to a Raman spectrometer 40 of the Raman spectroscopy subsystem 18. The Raman spectrometer thus receives target location information from the processor 26 so as to target specific potential viable organisms within the sample for targeted interrogation to measure the spectrum of viable organisms. In the schematic block diagram, the filter 34 is now relabeled as targeted filter 34B to designate that a sample on the filter 34 has been treated and targeted for interrogation.

In an exemplary implementation, each targeted cell, organism, feature, etc., within the sample that has been selected for targeted interrogation is moved under the Raman system where a spectrum of the target location is measured by the Raman spectrometer 40. The processor 26 analyzes the collected spectral information to make a preliminary assessment, e.g., to provide a preliminary identification of an organism positioned at the target location or to identify an organism within a small ambiguity. The analysis of the processor 26 repeats for each targeted location that is analyzed by the Raman spectrometer 40.

The processor 26 optionally further controls system level operation of the Raman spectroscopy subsystem 18, e.g., by instructing the automated Raman spectrometer 40 when to begin collecting spectra, where to target the sample substrate and/or by instructing the Raman spectrometer 40 as to how many spectra to collect. The processor 26 also optionally controls operational set points, e.g., operating parameters of the Raman spectrometer 40, e.g., by setting or otherwise influencing the magnification, and/or other parameters that influence the collection of spectral information, etc. In performing image analysis, the processor 26 may perform image data filtering, processing, classification, statistical analysis, feature or pattern recognition, etc., of the collected spectral information.

Upon spectral analysis, the targeted and treated filter 34B is located for processing at the visible imaging microscope subsystem 22. In exemplary implementations, the filter 34 is automatically relocated, e.g., via translation by the automation subsystem 20 e.g., using a linear translation stage or a rotational translation stage. In alternative exemplary implementations, the visible imaging microscope subsystem 22 receives the filter 34, e.g., via manual relocation. Still further, there may not be a need to physically relocate the filter 34, e.g., where both the Raman spectroscopy subsystem 18 and the visible imaging microscope subsystem 22 can both interact with the filter 34 positioned at a common physical location, e.g., using optics, etc.

The processor 26 analyzes the spectrum recorded by the Raman spectroscopy subsystem to make a preliminary identification of the targeted organisms within at least a small ambiguity of the organism under evaluation. The visible imaging microscope subsystem 22 provides a visual image of the targeted locations, e.g., particle(s), organism(s), etc., analyzed based upon the spectral data collected by the Raman spectroscopy subsystem 18. In an exemplary implementation, the visible imaging microscope subsystem 22 gives the operator a visual image of each targeted particle and allows the operator to make the final determination as to the nature of the particulate. In this regard, the processor 26, e.g., interacting via a suitable component of the I/O 30, conveys the preliminary assessment to the user so that the user can compare the results of the preliminary assessment with actual subjective user interpretation of the sample collected onto the filter 34. Moreover, the visual confirmation implemented by the user based upon the preliminary assessment need not be limited to a false positive confirmation of specifically selected target locations. Rather, the user is free to scan other portions of the sample collected onto the filter 34, e.g., to provide a check against false negative results or to evaluate locations for organisms or organism varieties that may not be within the capability of the processor 26 to properly identify.

Conventional techniques for identifying viable but not culturable organisms require an inspector to manually inspect fluorescing particles within a sample under test using microscopic identification. However, such tests are not always conclusive. For example, an operator typically has little time to make the determination of whether the fluorescence is an auto fluorescent amorphous particle or an organism. However, the system 10 according to various aspects of the present invention, allows the microbiologist operating the instrument to make more rapid and objective determinations. Moreover, limiting the particles under evaluation to viable particles may also be important in national defense and other applications to reduce false positives and provide some level of anti-spoofing to their systems. As such, the various aspects of the present invention are not limited to detecting specific viable organisms, but rather, for the identification of pathogens, allergens, bacteria, viruses, fungi, biological agents, other viable microorganisms and/or chemical particulates, etc.

In an exemplary implementation, the processor 26 implements data analysis algorithms that analyze the interrogation results, e.g., the spectral data collected by the Raman spectrometer 40, to determine whether biological or chemical particulates of interest are present in the sample area. The processor 26 also executes one or more appropriate action events based upon the analysis of the interrogation results. In an illustrative implementation, the processor 26 sounds an alarm or otherwise communicates an appropriate signal if biological or chemical particulates of interest are identified in the sample, e.g., within a targeted region of the filter 34. The processor 26 also optionally writes or otherwise stores logs, records or other indications to memory 28, e.g., with regard to the interrogation results and other relevant or otherwise desired information of interest.

Figure 3:
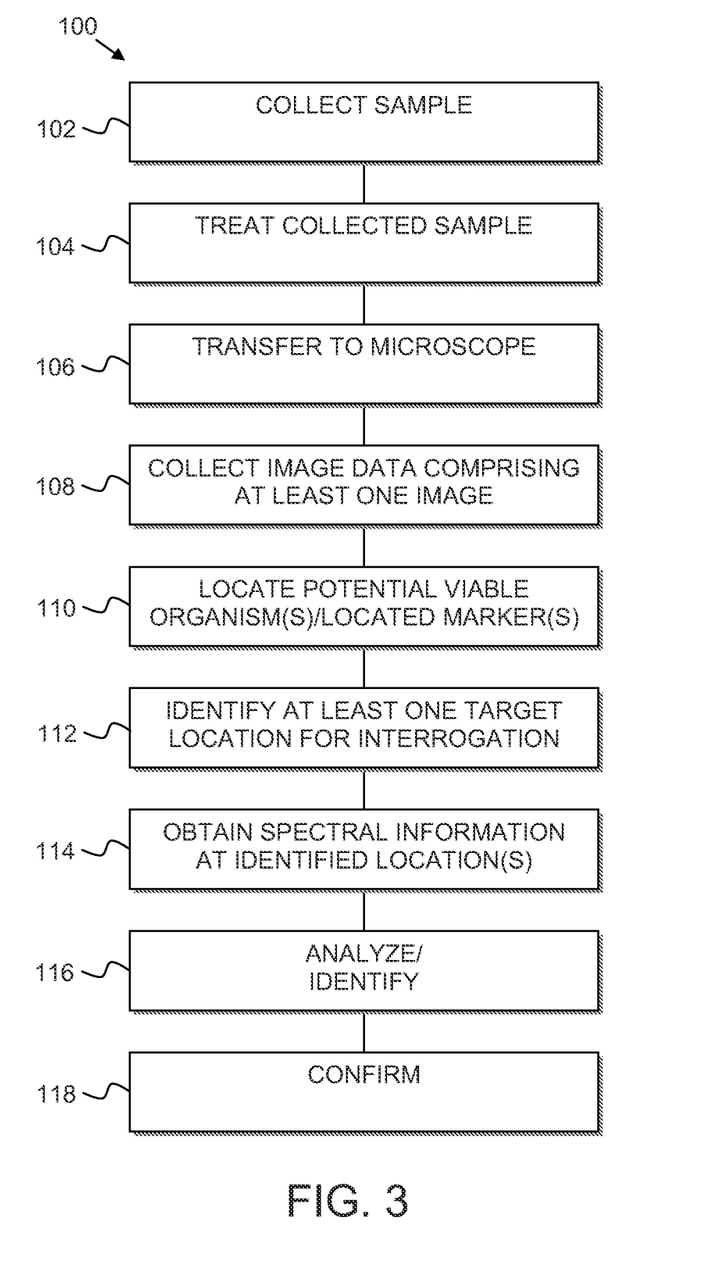
FIG. 3 is a flow chart illustrating a method of implementing fluorescence-cued identification according to various aspects of the present invention.

Referring to FIG. 3, a method 100 of implementing a fluorescence-cued Raman identification is illustrated that can be implemented, for example, by the processor 26 interacting with other components of the system 10. The method 100 comprises collecting a sample at 102. For example, an environmental sample, water sample, product sample, process sample, etc., may be collected onto a filter material. In an illustrative example, the sample is collected using an aerosol collector to sample the air and deposit the collected sample onto a non-Raman active membrane filter.

The method further comprises treating the collected sample at 104. The collected sample is treated with a reagent that identifies whether there are any organisms of interest within the sample, where a potential viable organism of interest is distinguishable based at least in part, by a marker produced as a result of a reaction between the reagent and the potential viable organism of interest. By way of a first illustration, the collected sample is treated with a viability stain to identify whether there are any organisms of interest collected within the sample, wherein an organism of interest is distinguishable based at least in part, because of the viability stain. Thus, for example, the collected sample is treated with a viability stain that fluoresces or otherwise causes viable organisms of interest to emit a glow that is stable for at least a finite period of time, when activated by a corresponding cell's processes. Organisms of interest within the sample are identified by automatically locating viable organisms within the collected sample through the activated stain's fluorescence, e.g., by detecting the glow using fluorescence detection within collected image data, as described in greater detail herein.

By way of another exemplary illustration, the sample is treated with a reagent that has a reporter dye that provides a specific spectral response to excitation that can be identified in corresponding image data, as also described in greater detail herein. By way of yet another exemplary illustration, the sample collected on the filter is treated using an assay, e.g., which includes suitable reagents and corresponding equipment so as to render one or more select types of living organisms detectable for at least a finite amount of time, where the detectable feature is detected within collected image data. As such, the assay may be targeted to at least one particular organism, e.g., that that leaves a marker at least temporarily, that is detected within collected image data, as described more fully herein.

The method still further comprises optionally transferring the filter to a microscope at 106, e.g., where relocation of the treated sample is necessary, and collecting image data of the treated sample using a microscope at 108. For example, an automatic microscope stage may be used to collect image data by automatically taking at least one focused image of the collected sample. The method also comprises locating at 110, any potential viable organisms of interest within the collected sample by utilizing image processing to automatically locate whether there are occurrences of the marker within at least one image of the collected sample. Further, the method comprises identifying at 112, at least one target location within the sample for spectral interrogation of a potential viable organism, each target location selected based upon the location of a corresponding instance of the marker within the sample that is derived from the collected image data. In this regard, each selected targeted location within the sample corresponds to a region sufficiently small to pinpoint a single potential viable organism within the sample for interrogation.

The method still further comprises obtaining spectral information of each identified target location within the sample at 114 and analyzing any obtained spectral information to automatically establish a preliminary identification of at least one corresponding located potential viable organism at 116, where each preliminary identification is made to at least a small ambiguity of the identification. In an exemplary implementation, a Raman spectrometer is utilized to collect a Raman spectrum for each target location, e.g., to measure the spectrum of each located potential viable organism. Image processing is then utilized to automatically locate any potential viable organisms on the filter membrane, e.g., by targeting locations on the membrane identified by a corresponding marker associated with the reagent treatment, such that each marked organism may be analyzed through targeted interrogation by a Raman system to collect spectral data corresponding to each targeted location(s).

The method still further comprises confirming the identification at 118 by providing information related to the result of the preliminary identification for a final confirmation by a user. As an example, the spectrums of any located viable organisms measured by the Raman spectrometer are automatically analyzed to establish a preliminary identification of any located viable organism(s)/particulate(s), etc., or to identify any viable organism(s)/particulate(s) within a small ambiguity of the identification. The system then provides information related to the viable organisms for final determination, e.g., by providing the collected sample to a visible microscope for user confirmation of the preliminary identification results, by providing an opportunity to the operator to view at least one visual image of the located viable organisms to an operator for verification of the automatically generated preliminary identification, so that the operator may make the final determination as to the identification/classification of the targeted viable organism(s)/particulate(s), etc.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention.

Having thus described the invention of the present application in detail and by reference to embodiments thereof, it will be apparent that modifications and variations are possible without departing from the scope of the invention defined in the appended claims.

What is claimed is:

1. A system for identifying organisms, comprising:
   a collection subsystem that collects a sample onto a filter;
   a reagent treatment subsystem that receives the sample from the collection subsystem and treats the sample collected by the collection subsystem using a reagent that identifies whether there are any organisms of interest within the sample, wherein a potential viable organism of interest is distinguishable based at least in part, by a marker produced as a result of a reaction between the reagent and the potential viable organism of interest;

a fluorescence imaging subsystem that receives the treated sample from the reagent treatment subsystem and that automatically takes at least one image of the collected sample;

a Raman spectroscopy subsystem that receives the sample from the fluorescence subsystem and that measures the spectrum of potential viable organisms that are located based upon at least one image of the collected sample;

a visible imaging microscope subsystem that provides a visual image of any organisms analyzed by the Raman spectroscopy subsystem; and a processor that performs image processing to locate potential viable organisms within the sample, which are targeted by the Raman spectroscopy subsystem, the processor further analyzes the spectrum recorded by the Raman spectroscopy subsystem to make a preliminary identification of the targeted organisms for confirmation by a user using the visible imaging microscope subsystem, the processor determines the target locations based upon the identification of markers located within at least one image, the processor communicates the preliminary identification to a user, the processor relinquishes control of the visual imaging microscope subsystem for the user to scan the target location and non-target locations of the collected sample to make a subjective identification and to compare the preliminary identification with the subjective identification.

2. The system according to claim 1, further comprising an automation stage that automatically transports the filter between at least two subsystems.

3. The system according to claim 1, wherein the Fluorescence imaging subsystem, Raman spectroscopy subsystem, automated stage subsystem and visible imaging microscope subsystem are integrated into a Raman microscope.

4. The system according to claim 1, wherein the collection subsystem comprises an aerosol collector that collects the sample from the ambient air, and the filter comprises a non-Raman active membrane filter material that receives the sample collected by the collector.

5. The system according to claim 1, wherein the reagent treatment subsystem treats the sample collected by the collection subsystem using a reagent implemented as a viability stain that causes viable organisms to emit a glow for at least a finite amount of time, where the glow is detectable by fluorescence detection within the collected image data.

6. The system according to claim 1, wherein the reagent treatment subsystem treats the sample collected by the collection subsystem using a reagent implemented as a reporter dye that provides a specific spectral response to excitation that can be identified in the corresponding image data.

7. The system according to claim 1, wherein the fluorescence imaging subsystem comprises an automated microscope that takes at least on image under the control of the processor, where the processor further utilizes image processing to automatically locate whether there are occurrences of the marker within at least one image of the collected sample.

8. The system according to claim 1, wherein the Raman spectroscopy subsystem comprises a Raman spectrometer that receives target location information from the processor so as to target specific potential viable organisms within the sample for targeted interrogation to measure the spectrum of viable organisms.

9. The system according to claim 1, wherein the processor analyzes the spectrum recorded by the Raman spectroscopy subsystem to make a preliminary identification of the targeted organisms within at least a small ambiguity of the organism under evaluation.

10. The system according to claim 1, further comprising a memory device and at least one input output device coupled to the processor for communicating image data to external sources.

11. A method of identifying organisms of interest comprising:

collecting a sample;

treating the collected sample with a reagent that identifies whether there are any viable microorganisms of interest within the sample, wherein a potential viable microorganism of interest is distinguishable based at least in part, by a marker produced as a result of a reaction between the reagent and the potential viable microorganism of interest;

collecting image data of the sample using a microscope;

locating any potential viable microorganisms of interest within the collected sample by utilizing image processing to automatically locate whether there are occurrences of the marker within at least one image of the collected sample;

identifying at least one target location within the sample for spectral interrogation of a potential viable microorganism of interest, each target location selected based upon the location of a corresponding instance of the marker within the sample that is derived from the collected image data;

obtaining spectral information of each identified target location within the sample by using a Raman spectrometer to collect a Raman spectrum through targeted interrogation at each identified location;

analyzing any spectral information obtained from the Raman spectrometer to automatically establish a preliminary identification of at least one corresponding located viable microorganism, each preliminary identification made to at least a small ambiguity of the identification;

providing information related to the result of the preliminary identification to a user;

generating a subjective identification based at least in part on an analysis of the collected sample at the identified target location; and comparing the preliminary identification with the subjective identification for a final confirmation.

12. The method according to claim 11, wherein collecting a sample comprises:

collecting the sample using an aerosol collector to sample the ambient air and deposit the collected sample onto a non-Raman active membrane filter.

13. The method according to claim 11, wherein treating the collected sample, comprises:

treating the sample with a viability stain that causes viable organisms to emit a glow for at least a finite amount of time, where the glow is detectable by fluorescence detection within the collected image data.

14. The method according to claim 11, wherein treating the collected sample, comprises:

treating the sample with a reagent that has a reporter dye that provides a specific spectral response to excitation that can be identified in the corresponding image data.

15. The method according to claim 11, wherein treating the collected sample, comprises:
 treating the sample with an assay that renders any living organism detectable for at least a finite amount of time, where the detectable feature is detected within the collected image data.

16. The method according to claim 11, wherein treating the collected sample, comprises:
 treating the sample with an assay that is targeted to at least one particular organism that leaves a marker detected within the collected image data.

17. The method according to claim 11, wherein collecting image data of the sample using the microscope, comprises:
 automatically taking at least one focused image of the collected sample.

18. The method according to claim 11, wherein identifying at least one target location within the sample for spectral interrogation of a potential viable organism, comprises:
 selecting a targeted location within the sample that corresponds to a region sufficiently small to pinpoint a single potential viable organism within the sample for interrogation, and obtaining spectral information further comprises using a Raman spectrometer to collect a Raman spectrum of the pinpointed organism.

19. The method according to claim 11, wherein generating the subjective identification further includes generating the subjective identification based on an analysis of the collected sample at non-target locations of the collected sample and the identified target locations.

20. The method according to claim 11, wherein providing information related to the result of the preliminary identification for a final confirmation by a user, comprises:
 providing the collected sample to a visible microscope for user confirmation of the preliminary identification results.

* * * * *